(12) United States Patent
Pullen

(10) Patent No.: US 8,629,086 B2
(45) Date of Patent: Jan. 14, 2014

(54) COMPOSITIONS AND METHODS FOR THE CONTROL OF NEMATODES AND SOIL BORNE DISEASES

(75) Inventor: Erroll M. Pullen, Wisteria Close (ZA)

(73) Assignee: Oro Agri, Inc., Trophy Club, TX (US)

( * ) Notice: Subject to any disclaimer, the term of this patent is extended or adjusted under 35 U.S.C. 154(b) by 407 days.

(21) Appl. No.: 12/585,232

(22) Filed: Sep. 9, 2009

(65) Prior Publication Data

US 2010/0144534 A1 Jun. 10, 2010

Related U.S. Application Data

(63) Continuation-in-part of application No. 12/449,358, filed as application No. PCT/US2008/001530 on Feb. 6, 2008.

(60) Provisional application No. 60/899,625, filed on Feb. 6, 2007.

(51) Int. Cl.
*A01N 27/00* (2006.01)

(52) U.S. Cl.
USPC ............................................... 504/357

(58) Field of Classification Search
None
See application file for complete search history.

(56) References Cited

U.S. PATENT DOCUMENTS

| | | | |
|---|---|---|---|
| 3,584,119 A | 6/1971 | Langley | |
| 4,039,588 A | 8/1977 | Wilson et al. | |
| 4,049,828 A * | 9/1977 | Cole | 514/703 |
| 4,379,168 A | 4/1983 | Dotolo | |
| 4,610,881 A | 9/1986 | Bechgaard | |
| 4,978,686 A * | 12/1990 | Sotome | 514/698 |
| 5,087,353 A | 2/1992 | Todd et al. | |
| 5,110,804 A | 5/1992 | Lee | |
| 5,118,506 A | 6/1992 | Eichoefer | |
| 5,143,939 A | 9/1992 | Browning | |
| 5,330,671 A | 7/1994 | Pullen et al. | |
| 5,374,600 A | 12/1994 | Hozumi et al. | |
| 5,389,257 A | 2/1995 | Todd et al. | |
| 5,444,078 A | 8/1995 | Yu et al. | |
| 5,527,482 A | 6/1996 | Pullen et al. | |
| 5,641,847 A | 6/1997 | Hozumi et al. | |
| 5,679,351 A * | 10/1997 | Walter et al. | 424/725 |
| 5,693,344 A | 12/1997 | Knight et al. | |
| 5,744,137 A | 4/1998 | Stone | |
| 5,753,593 A | 5/1998 | Pullen et al. | |
| 5,863,456 A | 1/1999 | Pullen | |
| 5,871,765 A | 2/1999 | Johnson et al. | |
| 5,876,622 A | 3/1999 | Pullen et al. | |
| 5,885,600 A | 3/1999 | Blum et al. | |
| 5,900,243 A | 5/1999 | Yoder et al. | |
| 5,948,743 A | 9/1999 | Fonsny et al. | |
| 5,958,287 A | 9/1999 | Pullen | |
| 5,977,186 A | 11/1999 | Franklin | |
| 6,093,856 A | 7/2000 | Cripe et al. | |
| 6,124,366 A | 9/2000 | Pullen et al. | |
| 6,130,253 A | 10/2000 | Franklin et al. | |
| 6,248,710 B1 | 6/2001 | Bijsterbosch et al. | |
| 6,251,951 B1 | 6/2001 | Emerson et al. | |
| 6,258,369 B1 * | 7/2001 | Pullen | 424/405 |
| 6,277,389 B1 | 8/2001 | Pullen | |
| 6,455,086 B1 | 9/2002 | Trinh et al. | |
| 6,500,445 B1 | 12/2002 | Pullen | |
| 6,514,512 B1 | 2/2003 | Puterka et al. | |
| 6,582,712 B2 | 6/2003 | Pullen | |
| 6,689,342 B1 | 2/2004 | Pan et al. | |
| 7,294,341 B2 | 11/2007 | Pullen | |
| 7,341,735 B2 | 3/2008 | Pullen | |
| 8,092,817 B2 | 1/2012 | Pullen et al. | |
| 2003/0035852 A1 | 2/2003 | Pullen | |
| 2003/0060379 A1 | 3/2003 | Souter et al. | |
| 2003/0224939 A1 | 12/2003 | Miles | |
| 2004/0138176 A1 | 7/2004 | Miles | |
| 2004/0242428 A1 | 12/2004 | Pullen | |
| 2008/0064603 A1 | 3/2008 | Pullen | |
| 2008/0070787 A1 | 3/2008 | Pullen | |
| 2008/0166437 A1 | 7/2008 | Rosskopf et al. | |
| 2008/0214400 A1 | 9/2008 | Pullen | |
| 2010/0144534 A1 | 6/2010 | Pullen | |

FOREIGN PATENT DOCUMENTS

| | | | | |
|---|---|---|---|---|
| EP | 0943239 a1 * | 9/1999 | | A01N 27/00 |
| WO | 9639846 | 12/1996 | | |
| WO | 9716975 | 5/1997 | | |
| WO | 9802044 | 1/1998 | | |
| WO | 0049865 A2 | 8/2000 | | |
| WO | WO0049865 A1 * | 8/2000 | | |
| WO | 0113726 | 3/2001 | | |
| WO | 0126457 A2 | 4/2001 | | |
| WO | 03020024 | 3/2003 | | |
| WO | 03056917 A2 | 7/2003 | | |
| WO | WO03056917 A1 * | 7/2003 | | A01N 25/00 |
| WO | 2005070213 A2 | 8/2005 | | |
| WO | 2006052228 | 5/2006 | | |
| WO | WO 2006052228 A1 * | 5/2006 | | |
| WO | 2008097553 | 8/2008 | | |
| WO | 2011031287 | 3/2011 | | |

OTHER PUBLICATIONS

Bauske et al., Management of Meloidogyne incognita on cotton by use of botanical aromatic compounds, Nematropica 24: 142-150 (1994).*

Chery Lin, 2007, downloaded Oct. 18, 2012 from http://cherylin.co.uk/chemical-constituents-essential-oils-may.pdf.*

Tripathi N. N. et al., "Toxicity of Some Terpenoids Against Fungi Infesting Fruits and Seeds of Capsicum-Annuum During Storate", Phytopatologische Zeitschrift, 1984, pp. 328-35, vol. 110, Vertag Paul Parey, Berlin, DE.

* cited by examiner

*Primary Examiner* — Abigail Fisher
*Assistant Examiner* — Thor Nielsen
(74) *Attorney, Agent, or Firm* — Millbank, Tweed, Hadley & McCloy LLP

(57) ABSTRACT

The instant invention relates to compositions and methods for the control of nematodes and soil borne diseases using compositions comprising high terpene containing oils and one or more surfactants. The invention also relates to methods for increasing the wetted soil volume available for water utilization by plant roots using the disclosed compositions.

41 Claims, 5 Drawing Sheets
(5 of 5 Drawing Sheet(s) Filed in Color)

COMPOSITIONS AND METHODS FOR THE CONTROL OF NEMATODES AND SOIL BORNE DISEASES

The instant application is a continuation-in-part of co-pending U.S. application Ser. No. 12/449,358 which is a national stage application based on PCT/US2008/01530 filed Feb. 6, 2008, which claims priority to U.S. Provisional Application 60/899,625 filed Feb. 6, 2007, the disclosures of which are hereby incorporated by reference herein in their entireties.

FIELD OF THE INVENTION

The instant invention relates to compositions and methods for the control of nematodes and soil borne diseases using compositions comprising high terpene containing oils and one or more surfactants. The invention also relates to methods for increasing the wetted soil volume available for water utilization by plant roots using the disclosed compositions. All references, patents and printed publications cited herein are hereby incorporated by reference in their entireties.

BACKGROUND

"Roundworms" or "nematodes" (phylum Nematoda) are the most diverse phylum of pseudocoelomates, and one of the most diverse of all animals. Over 80,000 species have been described, of which over 15,000 are parasitic. It has been estimated that the total number of described and undescribed roundworms might be more than 500,000. Unlike cnidarians or flatworms, roundworms have a digestive system that is like a tube at both ends.

Nematodes have successfully adapted to nearly every ecological niche from marine to fresh water, from the polar regions to the tropics, as well as the highest to the lowest of elevations. They are ubiquitous in freshwater, marine, and terrestrial environments, where they often outnumber other animals in both individual and species counts, and are found in locations as diverse as Antarctica and oceanic trenches. They represent, for example, 90% of all life on the seafloor of the Earth. The many parasitic forms include pathogens in most plants and animals (including humans.) Depending on the species, a nematode may be beneficial or detrimental to plant health.

From an agricultural perspective, there are two categories of nematode: predatory ones, which will kill garden pests like cutworms; and pest nematodes, like the root-knot nematode, which attack plants.

Predatory nematodes can be purchased as an organic form of pest control.

Rotations of plants with nematode-resistant species or varieties is one means of managing parasitic nematode infestations. For example, marigolds, grown over one or more seasons (the effective is cumulative), can be used to control nematodes. Another is treatment with natural antagonists such as the fungus *Gliocladium roseum*. Chitosan is a natural biocontrol that elicits plant defense responses to destroy parasitic cyst nematodes on roots of sobyean, corn, sugar beets, potatoes and tomatoes without harming beneficial nematodes in the soil.

Nematicides are agents that may be used to kill or control nematodes. One common nematicide is obtained from neem cake, the residue obtained after cold-pressing the fruit and kernels of the neem tree. Known by several names in the world, the tree has been cultivated in India since ancient times and is now widely distributed throughout the world. Nematophagous fungi, a type of carnivorous fungi, can be also be useful in controlling nematodes, *Paecilomyces* is one example.

Prior to 1985, the persistent halocarbon DBCP was a widely used nematicide and soil fumigant. However, it was banned from use after being linked to sterility among male farm workers. Aside from chemicals, soil steaming can be used to kill nematodes. Super-heated steam may be induced into the soil which causes almost all organic material to deteriorate.

In spite of attempts to control nematodes and other soil borne diseases, there remains a significant unmet need for effective nematicidal and soil borne disease controlling compositions to control and prevent unwanted nematode pests and other soil borne diseases.

SUMMARY OF THE INVENTION

The present invention is directed, in certain embodiments, to methods of killing plant pests that are present in soil. The target pests are the causative agents of one or more soil borne diseases that affect plants. In certain preferred embodiments, the pests include but are not limited to Nematodes, *Phytophthora, Fusarium, Pythium, Rhizoctonia, Sclerotinia, Erwinia* and *Verticillium*. The methods of the invention involve the step of selecting soil in need of treatment and applying an effective amount of a composition comprising one or more surfactants and one or more high terpene containing oils to the soil in need of treatment to thereby kill the plant pests in the soil that has been selected for treatment.

In certain embodiments, the selection of soil step comprises identifying soil containing any one of the target pests present in an amount sufficient to harm or reduce the growth of a plant growing in the soil. In certain embodiments, the selection of soil step comprises identifying soil containing any one of said pests present in an amount sufficient to reduce the yield of a plant growing in the soil.

In certain embodiments, the identification of soil in need of treatment is done by determining, based on a prior planting in the soil, that any one of said pests are present in the soil in an amount sufficient to harm plants growing in the soil or reduce the yield or the growth of plants grown in said soil.

In certain preferred embodiments, the plant pest to be killed in the soil is *Phytophthora*. In certain preferred embodiments, the plant pest to be killed in the soil is root-knot nematode.

In certain embodiments, the invention is directed to methods for increasing wetted soil volume such that there is an increased amount of water available for uptake by plant roots growing in the soil. In certain embodiments, the method comprises selecting soil in need of treatment and applying an effective amount of a composition comprising one or more surfactants and one or more high terpene based oils to the soil in need of treatment to thereby increase wetted soil volume such that there is an increased amount of water available for water uptake by plant roots growing in the soil compared to untreated soil.

In certain embodiments, the lateral movement of water in treated soil is increased compared to the lateral movement of water in soil that has not been subjected to treatment.

In certain embodiments, the treatment increases the amount of water available to a plant growing in said soil by increasing the amount of water in the root zone of the plant compared to soil that has not been subjected to the treatment.

In certain embodiments, the treated soil has at least 33% more wetted soil volume available for water uptake by the plant roots compared to untreated soil. In certain embodiments, the treated soil has at least 25% more wetted soil volume available for water uptake by the plant roots compared to untreated soil.

In certain embodiments, the invention is directed to methods comprising the steps of providing a concentrate comprising one or more surfactants and one or more high terpene containing oils; injecting said concentrate into a drip irrigation system to thereby dilute said concentrate; and applying said diluted concentrate to soil via said drip irrigation system. In certain embodiments, the concentrate is applied at a rate of between about 2 quarts to about 5 gallons per acre. In certain embodiments, injectors are used either at a central point of the irrigation system on the farm, or when a specific block has to receive a treatment, growers may use localized injectors at the block. The injectors at the central point where the pump is, are mostly powered by electricity, whereas the injectors that do not have electricity at the site may use the pressure of a small amount of water that is expelled from the system to power them. The injectors may be combined with a tank to hold the product. Growers may have the injector systems on wheels that can be pulled around to wherever it is needed in a block. This reduces costs by having one system for many sites.

In certain embodiments, the invention is directed to drip irrigation systems wherein the water in said drip irrigation system comprises one or more surfactants and one or more high terpene containing oils. In certain embodiments, the water in said drip irrigation system is delivered directly to the soil and is not applied directly to the plant or any part of the plant. In certain embodiments the water is delivered to soil prior to planting. In certain embodiments, the water is delivered to soil after planting. In certain embodiments, the planting comprises transgenic plants. In certain embodiments, the planting comprises non-transgenic plants.

In certain embodiments, the invention is directed to methods of increasing uniformity of water delivery by the drippers in a drip irrigation system comprising the steps of providing a concentrate comprising one or more surfactants and one or more high terpene containing oils; injecting said concentrate into a drip irrigation system to thereby dilute said concentrate; applying said diluted concentrate to soil via said drip irrigation system wherein the uniformity of water delivery in said drip irrigation system is increased compared to the water delivery of the drip irrigation system prior to treatment with the concentrate.

In certain embodiments, the invention is directed to methods of demineralizing a drip irrigation system comprising the steps of providing a concentrate comprising one or more surfactants and one or more high terpene containing oils; injecting said concentrate into a drip irrigation system to thereby dilute said concentrate; applying said diluted concentrate to soil via said drip irrigation system wherein the drip irrigation system contains less mineral deposit or scale compared to the drip irrigation system prior to treatment with the concentrate. The methods of the invention improve the water use efficiency of drip irrigation systems.

In certain preferred embodiments, the volume of water delivered by individual drippers in the drip irrigation system prior to treatment with said concentrates of the invention varies by at least 10% or at least 20% or at least 30% or at least 35% when said drippers are compared to each other.

In certain embodiments, the compositions of the invention are applied directly to the soil and not to the plant or any part of the plant. In certain preferred embodiments, the compositions of the invention are applied via a drip irrigation system. In certain embodiments, the compositions of the invention are applied to the soil prior to planting via drip irrigation. In certain embodiments, the compositions are applied to the soil via drip irrigation after planting.

In certain embodiments, the compositions of the invention are applied via sprinkler irrigation. In certain embodiments, the compositions of the invention are applied via a MICROJET® sprinkler. In certain embodiments, the compositions of the invention are applied to the soil prior to planting via sprinkler irrigation. In certain embodiments, the compositions are applied to the soil via sprinkler irrigation after planting.

In certain embodiments, the invention is directed to compositions comprising one or more surfactants and one or more high terpene containing oils. In certain embodiments, the one or more high terpene containing oil is a citrus oil. In certain embodiments, the high terpene containing oil is selected from the group consisting of orange oil, lemon oil, lime oil, grapefruit oil and tangerine oil. In a preferred embodiment, the high terpene containing oil is cold pressed orange oil.

In certain embodiments, the composition further comprises borax. In certain embodiments, the composition is a concentrate comprising from about 0.5% by weight to about 5% by weight borax. In certain embodiments, the concentrate comprises from about 1.0% to about 4.5% by weight borax. In certain embodiments, the concentrate comprises about 1.5% to about 4.0% by weight borax. In certain embodiments, the concentrate comprises about 2.0% to about 3.5% by weight borax. In certain preferred embodiments, the concentrate comprises about 2.5% to about 3.0% by weight borax.

In certain embodiments, the composition further comprises a fertilizer. In certain embodiments, the composition may further comprise a seaweed extract.

In certain embodiments, the composition further comprises micro-nutrients.

In certain embodiments, the composition further comprises propylene glycol. In certain embodiments, the composition is a concentrate comprising from about 5% by weight to about 10% by weight propylene glycol. In certain embodiments, the concentrate comprises from about 6% to about 9% by weight propylene glycol. In certain embodiments, the concentrate comprises about 8% to about 9% propylene glycol. In certain preferred embodiments, the concentrate comprises about 8.8% propylene glycol.

In certain embodiments, the composition further comprises sodium laureth sulfate. In certain embodiments, the composition is a concentrate comprising from about 3% by weight to about 10% by weight sodium laureth sulfate. In certain embodiments, the concentrate comprises from about 4% to about 9% by weight sodium laureth sulfate. In certain embodiments, the concentrate comprises about 5% to about 7% sodium laureth sulfate. In certain preferred embodiments, the concentrate comprises about 6% sodium laureth sulfate. In certain preferred embodiments, the sodium laureth sulfate is Calfoam ES-603.

In certain embodiments, the composition further comprises secondary alcohol ethoxylate. In certain embodiments, the composition is a concentrate comprising from about 10% by weight to about 30% by weight secondary alcohol ethoxylate. In certain embodiments, the concentrate comprises from about 15% to about 25% by weight secondary alcohol ethoxylate. In certain embodiments, the concentrate comprises about 18% to about 22% secondary alcohol ethoxylate. In certain preferred embodiments, the concentrate comprises about 20% secondary alcohol ethoxylate. In certain preferred embodiments, the secondary alcohol ethoxylate is Tergitol 15-S-9.

In certain embodiments, the composition further comprises urea. In certain embodiments, the composition is a concentrate comprising from about 0.1% by weight to about 2.0% by weight urea. In certain embodiments, the concentrate comprises from about 0.5% to about 1.5% by weight urea. In certain embodiments, the concentrate comprises about 0.8% to about 1.2% urea. In certain preferred embodiments, the concentrate comprises about 1.0% urea.

In certain embodiments, the composition further comprises tetrasodium ethylenediaminetetra-acetic acid (EDTA). In certain embodiments, the composition is a concentrate comprising from about 0.1% by weight to about 2.0% by weight EDTA. In certain embodiments, the concentrate comprises from about 0.2% to about 1.5% by weight EDTA. In certain embodiments, the concentrate comprises about 0.3% to about 1.0% EDTA. In certain preferred embodiments, the concentrate comprises about 0.5% EDTA. In certain preferred embodiments, the EDTA is Versene 220.

In certain embodiments, the composition further comprises methyl paraben. In certain embodiments, the composition is a concentrate comprising from about 0.01% by weight to about 2.0% by weight methyl paraben. In certain embodiments, the concentrate comprises from about 0.02% to about 1.5% by weight methyl paraben. In certain embodiments, the concentrate comprises about 0.03% to about 1.0% methyl paraben. In certain preferred embodiments, the concentrate comprises about 0.1% methyl paraben. In certain preferred embodiments, the methyl paraben is a methyl ester of benzoic acid.

In certain embodiments, the composition further comprises propyl paraben. In certain embodiments, the composition is a concentrate comprising from about 0.01% by weight to about 2.0% by weight propyl paraben. In certain embodiments, the concentrate comprises from about 0.02% to about 1.5% by weight propyl paraben. In certain embodiments, the concentrate comprises about 0.03% to about 1.0% propyl paraben. In certain preferred embodiments, the concentrate comprises about 0.1% propyl paraben. In certain preferred embodiments, the propyl paraben is a propyl ester of benzoic acid.

In certain embodiments, the composition further comprises orange oil. In certain embodiments, the composition is a concentrate comprising from about 1% by weight to about 20% by weight orange oil. In certain embodiments, the concentrate comprises from about 2% to about 15% by weight orange oil. In certain embodiments, the concentrate comprises about 5% to about 12% orange oil. In certain preferred embodiments, the concentrate comprises about 10% orange oil. In certain preferred embodiments, the orange oil is Valentia orange oil. In still further preferred embodiments, the orange oil is cold pressed orange oil.

In certain embodiments, the composition further comprises ethyl alcohol. In certain embodiments, the composition is a concentrate comprising from about 1% by weight to about 15% by weight ethyl alcohol. In certain embodiments, the concentrate comprises from about 2% to about 10% by weight ethyl alcohol. In certain embodiments, the concentrate comprises about 3% to about 7% ethyl alcohol. In certain preferred embodiments, the concentrate comprises about 5.5% ethyl alcohol.

In certain embodiments, the composition further comprises citric acid. In certain embodiments, the composition is a concentrate comprising from about 0.01% by weight to about 2.0% by weight citric acid. In certain embodiments, the concentrate comprises from about 0.02% to about 1.5% by weight citric acid. In certain embodiments, the concentrate comprises about 0.03% to about 1.0% citric acid. In certain preferred embodiments, the concentrate comprises about 0.1% citric acid.

In certain embodiments, the composition further comprises an insecticide, fungicide, herbicide, nematicide or acaricide.

DESCRIPTION OF THE FIGURES

The patent or application file contains at least one drawing executed in color. Copies of this patent or patent application publication with color drawing(s) will be provided by the Office upon request and payment of the necessary fee.

Figure 1:
FIG. 1: Leaves are providing excellent coverage protection from sunburn (treated). Compared with untreated control, the *Phytophthora* has stopped spreading to other plants and increased growth is observed. Maximum height of plants is approximately 17 inches. Observed bloom count of 8% over the untreated block (bloom count is the number of flowers per unit such as per plant or a certain distance in the row). Treated plants provide excellent coverage protection from sunburn. Overall plant health as seen in the picture is excellent.

FIG. 2: In treated plants, peppers inside leaf cover are difficult to see.

FIG. 3: Untreated plants are same age as other pictures. Notice how hard plant leaves look. Maximum height of plants is 13 inches.

FIG. 4: Untreated plants do not provide enough shade to protect the peppers against sunburn. Sunburned pepper appears yellow.

FIG. 5: Untreated plants. More sunburn. Notice squatting of plants. Squatting as referred to here is a lack of mainly vertical growth due a problem in the root system causing stress in the plant. This may be any relevant disease, poor soil conditions and water stress.

DETAILED DESCRIPTION

The present invention is directed, in certain embodiments, to the control, killing or prevention of nematodes and soil borne diseases. Such soil borne diseases include but are not limited to *Fusarium, Pythium, Rhizoctonia, Sclerotinia, Erwinia* and *Verticillium*. The compositions disclosed herein have been found to be surprisingly and unexpectedly effective in killing plant pathogenic nematodes as well as organisms that are the causative agents of soil borne diseases. It has additionally been found that the disclosed compositions significantly increase the wetted soil volume available for water utilization by plant roots in soil treated with the compositions.

Applicant has found that the compositions disclosed herein kill nematodes when applied directly to soil, this was not expected and very surprising.

Applicant has also found that the compositions kill *Fusarium, Pythium, Rhizoctonia, Sclerotinia, Erwinia* and *Verticillium*, this was not expected and very suprising.

When applied via drip irrigation, the composition wets the treated soil in a more lateral fashion as opposed to forming more vertical channels. The result is that the wetted soil volume available for water utilization by plant roots is larger and drainage loss below the root zone is limited. This was not expected and very surprising.

Because the compositions increase the wetted soil volume available for water utilization by the plant, there is a larger reservoir of water available during periodic times of moisture stress like with daily fluctuations in water loss by the plant or during times of drought.

Any treatment that improves the ability of the root zone to expand and absorb water better during times of moisture stress, improves the growth and vigor of the whole plant, making it better able to withstand attacks by pests, including but not limited to, nematodes. Many above-ground pests including, but not limited to, mites increase their attacks and speed up their breeding rate when they perceive plants to be under stress. The plant being under stress is a sign to the pest that the food source might be depleted, triggering an increased breeding rate.
Figure 2:
Figure 3:
Figure 4:
Figure 5:

Improved growth and vigor of plants leads to more rapid expansion of the foliage area of plants, leading to an increase in the net assimilation rate and consequently the production of more photosynthetic products. This increases the production of seeds, fruits, edible foliage or plant parts that are useful like foliage of turf grass.

Plants that are under stress tend to favor reproductive development directed towards the formation of seeds as a last resort and neglect the development of other edible parts of the plant like fruit, apart from the seed, for which the plant is being produced. This includes but is not limited to, strawberries, stone fruit, pome fruit, tomatoes, peppers, cucurbit fruits. Plants that are specifically grown to produce seeds, like nuts, when grown under stress, have smaller seeds that are not desirable for marketing purposes.

The compositions of the invention, when injected into drip irrigation systems, improve the efficiency of the individual drippers in treated drip irrigation systems and make the volume of water delivered by the individual drippers in the drip irrigation system more uniform. In other words, after treatment with the compositions of the invention, dripper heads in a drip irrigation system deliver closer to the same amount of water to soil over the same time period. This increases the accuracy of the dripper volume and makes the drip irrigation system more efficient because it allows the grower to more accurately control the amount of water delivered to soil.

Individual drippers and the tubing in drip irrigation systems can sometimes become "clogged" due to mineralization or the creation of mineral deposits or scale inside the tubing and drippers. This can occur when certain nutrients are used over a period of time. In some drip irrigation systems, the water volume delivered by individual drippers in a drip irrigation systems can vary by as much as about 35% between different drippers. Variability between drippers can also occur when hard water is used which contains high levels of calcium and/or minerals and/or salts.

While not wishing to be bound by theory, one explanation for the improved uniformity of drip volumes between individual drippers after treatment of a drip irrigation system with the compositions of the invention is that the compositions dissolve mineral deposits or scale that can form over time within drip irrigations systems. Thus, the amount of mineral deposit or scale in the drip irrigation system is reduced upon treatment with the compositions of the invention. The result is that the drip irrigation system is less clogged, the flow of water is not as restricted and the openings in the drippers are less blocked or less obstructed.

As used herein, "demineralization" or "demineralizing" means that the amount of mineral deposit or scale present in a system is reduced compared to the system in question prior to treatment with the compositions of the invention.

One advantage to having uniformity of drip volume between individual drippers in a drip irrigation system is that growers are better able to control the amount of water to be delivered by the drippers to the soil. The is a surprising and unexpected property of the compositions of the invention.

As used herein, high terpene containing natural oil means those natural oils having a terpene content of at least 50 percent. It is preferable that the high terpene natural oil contains at least 65 percent terpene. Suitable high terpene containing natural oils includes oil from conifers such as citrus peel oils, preferably orange oil, grapefruit oil, lemon oil, lime oil, tangerine oil or pine oil. Of these, orange oil is preferred and cold pressed orange oil the most preferred. The preferred terpene content is from about 80 percent to about 95 percent and most preferred from about 85 percent to about 87 percent, all by weight. D'Limonene (Terpene of Citrus or other natural oils) may also be used.

As used herein, the terms "terpene" or "high terpene" refer to any of a class of chemical compounds that are widespread in nature, mainly in plants as constituents of essential oils. Many terpenes are hydrocarbons, but oxygen-containing compounds such as alcohols, aldehydes or ketones (terpenoids) are also found. Their building block is the hydrocarbon isoprene, $CH_2=C(CH_3)-CH=CH_2$. Certain terpene hydrocarbons have molecular formulas $(C_5H_8)_n$, and may be classified according to the number of isoprene units. When terpenes are modified chemically, such as by oxidation or rearrangement of the carbon skeleton, the resulting compounds are generally referred to as "terpenoids." As used herein, the term "terpene" includes all "terpenoids." Examples of monoterpenes are: pinene, nerol, citral, camphor, menthol, limonene. Examples of sesquiterpenes are: nerolidol, farnesol. Examples of diterpenes are: phytol, vitamin $A_1$. Squalene is an example of a triterpene, and carotene (provitamin $A_1$) is a tetraterpene.

In the context of methods of killing plant pests, as used herein, "soil in need of treatment" means soil that contains a causative agent, nematode, fungus, bacteria, virus or other pathogenic organism harmful to plants.

In the context of methods for increasing wetted soil volume, as used herein, "soil in need of treatment" means soil that has been subjected to drought conditions or arid conditions such that plants grown in said soil are stressed due to lack of sufficient available water in the root zones of said plants.

As used herein, "identifying soil containing any of the pests disclosed herein present in an amount sufficient to harm or reduce the growth of a plant growing in said soil" means soil that contains a causative agent, nematode, fungus, bacteria, virus or other pathogenic organism harmful to plants.

As used herein, the "root zone" of a plant means the entire area where roots are growing below a plant.

As used herein, the terms "pesticidal effect" and "pesticidal activity" mean any direct or indirect action on the target pest that results in reduced feeding damage on any part of the plant, including but not limited to the seeds, roots, shoots and foliage of plants as compared with untreated plants.

The terms "active against a (first or second) pest", also have the same meaning. Such direct or indirect effects include inducing death of the pest, repelling the pest from any part of the plant, including but not limited to seeds, roots, shoots and/or foliage, inhibiting feeding of the pest on, or the laying of its eggs on, the plant seeds, roots, shoots and/or foliage, and inhibiting or preventing reproduction of the pest.

"Plant pest" means any organism known to associate with plants and which, as a result of that association, causes a detrimental effect on the plant's health and vigor. Plant pests include but are not limited to fungi, bacteria, viruses, molds, insects, mites and nematodes or any other organism that causes a detrimental effect on the plant's health or vigor, excluding mammals, fish and birds.

The term "plant" as used herein encompasses whole plants and parts of plants such as roots, shoots, stems, leaves, buds, seedlings, germinated seeds and seed, as well as cells and tissues within the plants or plant parts.

The term "insecticidal activity" has the same meaning as pesticidal activity, except it is limited to those instances where the pest is an insect.

As used herein, the "shoots and foliage" of a plant are to be understood to be the shoots, stems, branches, leaves, buds and other appendages of the stems and branches of the plant after the seed has sprouted, including the roots of the plant. It is preferable that the shoots and foliage of a plant be understood to be those parts of the plant that have grown from the seed and/or shoots of a "mother" plant.

As used herein, the "region of the seed" is to be understood to be that region within about one inch of the seed.

The one or more high terpene (50% by weight or more) based oils, such as, but not limited to, citrus oil compositions of the present invention can be in the form of a liquid or solid solution; suspension; emulsion; emulsion concentrate; slurry of particles in an aqueous medium (e.g., water); wettable powder; wettable granules (dry flowable); dry granules; stake, or stick. The concentration of the active ingredients in the formulation is preferably about 0.5% to about 99% by weight (w/w), preferably 5-40%.

Preferably, the one or more high terpene (50% terpene by weight or more) based oils such as but not limited to citrus oil compositions of the invention may comprise from about 0.5% to about 99%, or preferably about 1% to about 30% one or more high terpene (50% terpene by weight or more) based oils such as but not limited to citrus oil by weight. In certain preferred embodiments, the one or more high terpene (50% terpene by weight or more) based oils such as but not limited to citrus oil compositions of the invention may comprise about 5% to about 20%, or about 12% to about 20% or about 12% to about 18% or about 10% citrus oil by weight.

Preferably, the one or more high terpene (50% terpene by weight or more) based oils such as but not limited to citrus oil compositions of the invention may comprise about 3% to about 90% by weight surfactant or any percent by weight within this range. Preferably, about 5% to about 20% by weight surfactant. When used as an adjuvant, the final surfactant concentration is preferably about 0.05% to about 0.8% by weight surfactant. In some embodiments, this may be from about 0.25% to about 0.33% by weight surfactant. In other embodiments, the surfactant is present at about 0.05% by weight to about 0.2% by weight and in other embodiments between about 0.025% to about 0.05%.

In certain embodiments, the one or more high terpene (50% terpene by weight or more) based oils such as but not limited to citrus oil compositions of the invention may further comprise one or more insecticides, fungicides, miticides, herbicides, nutrients, plant growth regulators and/or fertilizers. In these embodiments, the one or more high terpene (50% terpene by weight or more) based oils such as but not limited to citrus oil compositions of the invention may comprise about 0.5% to about 65% insecticides, fungicides, miticides, herbicides, nutrients, plant growth regulators and/or fertilizers by weight. In certain preferred embodiments, the one or more high terpene (50% terpene by weight or more) based oils such as but not limited to citrus oil compositions of the invention may comprise about 90% to about 99.99% insecticides, fungicides, miticides, herbicides, nutrients, plant growth regulators and/or fertilizers by weight.

In certain embodiments of the one or more high terpene (50% terpene by weight or more) based oils such as but not limited to citrus oil compositions contemplated herein, the pH of the composition is between about 6.0 to about 9.0 or preferably about 7.8 to about 8.0.

In certain embodiments, the one or more high terpene (50% terpene by weight or more) based oils such as but not limited to citrus oil compositions of the invention may be diluted with water prior to use. Preferably, the citrus oil compositions may be diluted by combining from about 1 part one or more high terpene (50% terpene by weight or more) based oils such as but not limited to citrus oil composition with about 2,000 parts water (1:2000); or about 2.5 parts citrus oil composition with about 100 parts water (2.5:100). In certain embodiments, when used with insecticides or fungicides, the compositions of the invention may be diluted with water by combining about 100 parts water with about 1 part of the composition (100:1) or any intervening dilution up to about 2000 parts water with about 1 part of the composition. When used as an adjuvant, the compositions of the invention may be combined with about 500 parts water with about 1 part composition or any intervening dilution up to about 2000 parts water or about 4000 parts water with about 1 part composition.

Other conventional inactive or inert ingredients can be incorporated into the citrus oil formulations. Such inert ingredients include but are not limited to: conventional sticking agents, dispersing agents such as methylcellulose (Methocel A15LV or Methocel A15C, for example, serve as combined dispersant/sticking agents for use in seed treatments), polyvinyl alcohol (e.g., Elvanol 51-05), lecithin (e.g., Yelkinol P), polymeric dispersants (e.g., polyvinylpyrrolidone/vinyl acetate PVP/VA S-630), thickeners (e.g., clay thickeners such as Van Gel B to improve viscosity and reduce settling of particle suspensions), emulsion stabilizers, surfactants, antifreeze compounds (e.g., urea), dyes, colorants, and the like.

Further inert ingredients useful in the present invention can be found in McCutcheon's, vol. 1, "Emulsifiers and Detergents," MC Publishing Company, Glen Rock, N.J., U.S.A., 1996. Additional inert ingredients useful in the present invention can be found in McCutcheon's, vol. 2, "Functional Materials," MC Publishing Company, Glen Rock, N.J., U.S.A., 1996.

Surfactants

The following compounds are provided as non-limiting examples of the surfactants:

Nonionic surfactants include agents such as sorbitan monolaurate, sorbitan monopalmitate, sorbitan sesquioleate, sorbitan trioleate, polyoxyethylene sorbitan monolaurate, polyoxyethylene sorbitan monostearate, polyethylene glycol monooleate, polyethylene glycol alkylate, polyoxyethylene alkyl ether, polyglycol diether, lauroyl diethanolamide, fatty acid iso-propanolamide, maltitol hydroxy fatty acid ether, alkylated polysaccharide, alkyl glucoside, sugar ester, oleophillic glycerol monostearate, self-emulsifiable glycerol monostearate, polyglycerol monostearate, polyglycerol alkylate, sorbitan monooleate, polyethylene glycol monostearate, polyoxyethylene sorbitan monooleate, polyoxyethylene cetyl ether, polyoxyethylene sterol, polyoxyethylene lanolin, polyoxyethylene bees wax, and polyoxyethylene hydrogenated castor oil; and the like.

Anionic surfactants include agents such as sodium stearate, potassium palmitate, sodium cetyl sulfate, sodium lauryl phosphate, sodium polyoxyethylene lauryl sulfate, triethanolamine palmitate, polyoxyethylene sodium lauryl phosphate, and sodium N-acyl glutamate; and the like.

Cationic surfactants include agents such as stearyl dimethylbenzyl ammonium chloride, stearyl trimethyl ammonium chloride, benzalkonium chloride, and laurylamine oxide; and the like.

Amphoteric surfactants such as alkylaminoethyl glycine chloride and lecithin; and the like.

CALFOAM® ES-603 is a clear liquid sodium salt of alcohol ethoxy sulfate with a faint alcohol odor. This biodegradable surfactant is pourable and pumpable at ambient temperatures and functions as a flash foamer and foam stabilizer in aqueous systems.

TERGITOL™ 15-S-9 Surfactant is known chemically as secondary alcohol ethoxylate. It is a non-ionic surfactant.

Citrus Oils and One or More High Terpene (50% Terpene by Weight or More) Based Oils Citrus oils include orange oil, lemon oil, lime oil, grapefruit oil and tangerine oil.

The one or more high terpene (50% by weight or more) based oils, such as but not limited to citrus oils, of the compositions and methods of the invention may be obtained by any method from the citrus fruit in question. In particular, citrus oils are obtained from the skin or peel of the fruit in question. Preferred methods of obtaining the citrus oil include but are not limited to cold pressing techniques. Examples of terpene containing oils that may be used in the compositions of the invention include, but are not limited to, pine oils and naturally occurring oils of plants that contain 50% terpene or more terpenes.

Insecticides, Miticides and Fungicides

The terms "insecticide", "miticide", "fungicide" and "adjuvant for other crop protection chemicals", include any agent used primarily for the control of insects and/or mites or fungi by preventing, destroying, repelling or mitigating any insects and/or mites or fungi which may be present in any environment whatsoever. These terms include the concepts of "acaricide" (agent used primarily in the control of plant-feeding mites, especially spider mites), "nematicide" (agent used primarily for the control of root-infesting nematodes on crop plants), "insect pheromone" (agent used primarily for the control of behavioral responses of insects).

Herbicides

The citrus oil compositions of the invention may also comprise one or more herbicides.

Fertilizers and Nutrients

The invention compositions may also comprise fertilizers and nutrients (e.g. nitrogen-, potassium- or phosphorus-containing fertilizers). Compositions comprising only granules of fertilizer incorporating, for example coated with, the citrus oil compositions are preferred. Such granules suitably contain up to 25% by weight of the citrus oil composition. The invention therefore also provides a fertilizer composition comprising a fertilizer and the citrus oil compositions disclosed herein.

Seaweed is a loose colloquial term encompassing macroscopic, multicellular, benthic marine algae. Seaweed extracts may be used as fertilizers. The term includes some members of the red, brown and green algae. A seaweed may belong to one of several groups of multicellular algae: the red algae, green algae, and brown algae. As these three groups are not thought to have a common multicellular ancestor, the seaweeds are a paraphyletic group. In addition, some tuft-forming bluegreen algae (Cyanobacteria) are sometimes considered as seaweeds.

Macronutrients required by plants can be divided into two groups, primary and secondary nutrients. The primary nutrients are nitrogen, phosphorus and potassium. Plants use large amounts of these nutrients for their growth and survival.

The secondary nutrients are calcium, magnesium and sulfur.

There are at least eight micro-nutrients essential to plant growth and health that are only needed in very small quantities. These are manganese, boron, copper, iron, chlorine, cobalt, molybdenum, and zinc. Some also consider sulfur a micronutrient. Though these are present in only small quantities, they are all necessary.

Boron is believed to be involved in carbohydrate transport in plants; it also assists in metabolic regulation. Boron deficiency will often result in bud dieback. Boron is also essential for pollen tube growth in plants.

Chlorine is necessary for osmosis and ionic balance; it also plays a role in photosynthesis.

Cobalt is essential to plant health. Cobalt is thought to be an important catalyst in nitrogen fixation. It may need to be added to some soils before seeding legumes.

Copper is a component of some enzymes and of vitamin A. Symptoms of copper deficiency include browning of leaf tips and chlorosis.

Iron is essential for chlorophyll synthesis, which is why an iron deficiency results in chlorosis.

Manganese activates some important enzymes involved in chlorophyll formation. Manganese deficient plants will develop chlorosis between the veins of its leaves. The availability of manganese is partially dependent on soil pH.

Molybdenum is essential to plant health. Molybdenum is used by plants to reduce nitrates into usable forms. Some plants use it for nitrogen fixation, thus it may need to be added to some soils before seeding legumes.

Zinc participates in chlorophyll formation, and also activates many enzymes. Symptoms of zinc deficiency include chlorosis and stunted growth.

TABLE 1

List of minimum and maximum elemental contents in liquid fertilizers

| Ingredient | Ingredient Symbol | Minimum g/kg | Maximum g/kg | Mininum % w/w | Maximum % w/w |
| --- | --- | --- | --- | --- | --- |
| Nitrogen | N | 51 | 96 | 5.1 | 9.6 |
| Phosphorus | P | 10 | 63 | 1 | 6.3 |
| Potassium | K | 32 | 83 | 3.2 | 8.3 |
| Calcium | Ca | 56.6 | 195 | 5.66 | 19.5 |
| Magnesium | Mg | 9 | 55 | 0.9 | 5.5 |
| Boron | B | 0.2 | 115 | 0.02 | 11.5 |
| Iron | Fe | 1 | 70 | 0.1 | 7 |
| Manganese | Mn | 0.5 | 90 | 0.05 | 9 |
| Molybdenum | Mo | 0.005 | 0.28 | 0.0005 | 0.028 |
| Zinc | Zn | 0.5 | 120 | 0.05 | 12 |
| Copper | Cu | 0.5 | 140 | 0.05 | 14 |
| Sulphur | S | 10 | 12.4 | 1 | 1.24 |

Plant Growth Regulators

Plant growth regulators, also known as plant hormones and phytohormones are chemicals that regulate plant growth. According to a standard animal definition, hormones are signal molecules produced at specific locations, that occur in very low concentrations, and cause altered processes in targeted cells at other locations. Plant hormones, on the other hand, are distinct from animal hormones, since they are often not transported to other parts of the plant and production is not limited to specific locations. Plants lack tissues or organs specifically for the production of hormones; unlike animals, plants lack glands that produce and secrete hormones that are then circulated around the body. Plant hormones shape the plant, affecting seed growth, time of flowering, the sex of flowers, senescence of leaves and fruits, they affect which tissues grow upward and which grow downward, leaf formation and stem growth, fruit development and ripening, plant longevity and plant death.

Plant Varieties and Crops

The citrus oil compositions disclosed herein are preferably used for agricultural and horticultural purposes in the form of a composition. The type of composition used in any instance will depend upon the particular purpose envisaged.

It is contemplated that the present methods can be used to protect the seeds, roots and/or the above-ground parts of field, forage, plantation, glasshouse, greenhouse, orchard or vineyard crops, grasses, turf, ornamentals, plantation, household or forest trees.

The plants that may be treated using the methods and compositions disclosed herein can be any species of plant. However, they are preferably the plant species that are agronomically or horticulturally important. In particular, the plant species can be corn, peanut, canola/rapeseed, soybean, cucurbits, crucifers, cotton, beets, rice, sorghum, sugar beet, wheat, barley, rye, sunflower, tomato, sugarcane, tobacco, oats, as well as other vegetable and leaf crops. In certain embodiments, the crops or plant species may include vineyards, citrus, pecans, almonds, all stone fruits, apples, pears, bananas, lawns, turf, home & garden and garden varieties of plants.

The plants may also be any ornamental plants, including but not limited to rose, tulip, violet, daffodil, gladiolus, lavender, lilies, narcissus, orchid, hyacinth, chrysanthemum, crocus, iris, peonies, zephyranthes, carnation, anthurium, gloxinia, azalea, poinsettia, ageratum, bamboo, begonia, camellia, dahlia, dianthus, geranium, impatiens, lilies of the valley and lobelia.

In one embodiment of the invention, the plant or seed is a non-transgenic plant or seed.

In another embodiment of the invention, the plant or seed is a transgenic plant or seed from which a transgenic plant can grow. The transgenic plants and seeds of the present invention are engineered to express a desirable characteristic and, in particular, to have at least one heterologous gene encoding for the expression of a protein that is pesticidally active and, in particular, has insecticidal activity. The heterologous gene in the transgenic plant or seed of the present invention can be derived from a microorganism such as *Bacillus, Rhizobium, Pseudomonas, Serratia, Trichoderma, Clavibacter, Glomus, Gliocladium* and mycorrhizal fungi. In particular, it is contemplated that the present methods are especially beneficial when the heterologous gene is one that is derived from a *Bacillus* sp. microorganism and the protein is active against corn rootworm.

It is also contemplated that the present methods are especially beneficial when the heterologous gene is one that is derived from a *Bacillus* sp. microorganism and the protein is active against European corn borer. A preferred *Bacillus* sp. microorganism is *Bacillus thuringiensis*. It is particularly preferred when the heterologous gene encodes a modified Cry3Bb delta-endotoxin derived from *Bacillus thuringiensis*.

Methods of Application

The compositions disclosed herein can be applied in a number of ways. In the most preferred method of application, the compositions disclosed herein are applied directly to the soil that has been selected for treatment. Application methods include drip irrigation, sprinkler irrigation, spraying, or dusting or applying as a cream or paste formulation, or applying as a vapor or as slow release granules.

The compositions may be applied using methods including but not limited to spraying, wetting, dipping, misting, drenching, showering, fogging, soaking, dampening, drizzling, dousing, aerial crop dusting via airplane or helicopter and splashing.

The compositions may be in the form of dustable powders or granules comprising the citrus oil compositions in dry form and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the citrus oil compositions or by pelleting a mixture of the citrus oil composition and powdered filler.

Compositions for dressing seed may include an agent (for example, a mineral oil) for assisting the adhesion of the citrus oil composition to the seed; alternatively the active ingredient can be formulated for seed dressing purposes using an organic solvent (for example, N-methylpyrrolidone, propylene glycol or N,N-dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the citrus oil composition in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The citrus oil compositions can be mixed in the dry state with a pyrotechnic mixture to form a composition suitable for generating in enclosed spaces a smoke containing the citrus oil compositions.

Alternatively, the citrus oil compositions may be used in micro-encapsulated form. They may also be formulated in biodegradable polymeric formulations to obtain a slow, controlled release of the citrus oil composition.

By including suitable additives, for example additives for improving the distribution, adhesive power and resistance to rain on treated surfaces, the citrus oil compositions can be better adapted for various utilities.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Seed Coatings

The one or more high terpene (50% terpene by weight or more) based oils such as but not limited to citrus oil compositions of the invention may be used as seed coatings. Useful seed coatings contain one or more binders and at least one of the subject citrus oil compositions. Binders that are useful in the present invention preferably comprise an adhesive polymer that may be natural or synthetic and is without phytotoxic effect on the seed to be coated. The binder may be selected from polyvinyl acetates; polyvinyl acetate copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

The amount of binder in the coatings of the invention can vary, but will be in the range of about 0.01 to about 25% of the weight of the seed, more preferably from about 0.05 to about 15%, and even more preferably from about 0.1% to about 10%.

The citrus oil formulations of the invention can optionally include a filler. The filler can be an absorbent or an inert filler, such as are known in the art, and may include woodflours, clays, activated carbon, sugars, diatomaceous earth, cereal flours, fine-grain inorganic solids, calcium carbonate, and the like. Clays and inorganic solids which may be used include calcium bentonite, kaolin, china clay, talc, perlite, mica, vermiculite, silicas, quartz powder, montmorillonite and mixtures thereof. Sugars which may be useful include dextrin and maltodextrin. Cereal flours include wheat flour, oat flour and barley flour.

The filler is selected so that it will provide a proper microclimate for the seed, for example the filler is used to increase the loading rate of the active ingredients and to adjust the control-release of the active ingredients. The filler can aid in the production or process of coating the seed. The amount of filler can vary, but generally the weight of the filler components will be in the range of about 0.05 to about 75% of the seed weight, more preferably about 0.1 to about 50% terpene, and even more preferably about 0.5% to 15%.

The exact amount of the combination of the active ingredients that is included in the coating is determined by one of skill in the art and will vary depending upon the size of the seed to be coated. The active ingredients of the coating must not inhibit germination of the seed and should be efficacious in protecting the seed and/or the plant during that time in the target insect's life cycle in which it causes injury to the seed or plant. In general, the coating will be efficacious for approximately 0 to 120 days after sowing.

The coating is particularly effective in accommodating high active ingredient loads, as can be required to treat typically refractory pests, such as corn root worm, while at the same time preventing unacceptable phytotoxicity due to the increased active ingredient load.

Optionally, a plasticizer can be used in the coating formulation. Plasticizers are typically used to make the film that is formed by the coating layer more flexible, to improve adhesion and spreadability, and to improve the speed of processing. Improved film flexibility is important to minimize chipping, breakage or flaking during storage, handling or sowing processes. Many plasticizers may be used, however, useful plasticizers include polyethylene glycol, glycerol, butylbenzylphthalate, glycol benzoates and related compounds. The range of plasticizer in the coating layer will be in the range of from about 0.1 to about 20% by weight.

Nematicides

A nematicide is a type of chemical pesticide used to kill parasitic nematodes (roundworms).

Nematodes

Plant parasitic nematodes include several groups causing severe crop losses. The most common genera are *Aphelenchoides* (foliar nematodes), *Ditylenchus, Globodera* (potato cyst nematodes), *Heterodera* (soybean cyst nematodes), *Longidorus, Meloidogyne* (root-knot nematodes), *Nacobbus, Pratylenchus* (lesion nematodes), *Trichodorus* and *Xiphinema* (dagger nematodes). Several phytoparasitic nematode species cause histological damage to roots, including the formation of visible galls (e.g. by root-knot nematodes), which are useful characteristics for their diagnosis in the field. Some nematode species transmit plant viruses through their feeding activity on roots. One of them is *Xiphinema* index, vector of GFLV (Grapevine Fanleaf Virus), an important disease of grapes.

Other nematodes attack bark and forest trees. The most important representative of this group is *Bursaphelenchus xylophilus*, the pine wood nematode, present in Asia and America and recently discovered in Europe.

Nematodes commonly parasitic on humans include ascarids (*Ascaris*), filarids, hookworms, pinworms (*Enterobius*) and whipworms (*Trichuris trichiura*). The species *Trichinella spiralis*, commonly known as the trichina worm, occurs in rats, pigs, and humans, and is responsible for the disease trichinosis. *Baylisascaris* usually infests wild animals but can be deadly to humans as well. *Haemonchus contortus* is one of the most abundant infectious agents in sheep around the world, causing great economic damage to sheep farms. In contrast, entomopathogenic nematodes parasitize insects and are considered by humans to be beneficial.

One form of nematode is entirely dependent upon fig wasps, which are the sole source of fig fertilization. They prey upon the wasps, riding them from the ripe fig of the wasp's birth to the fig flower of its death, where they kill the wasp, and their offspring await the birth of the next generation of wasps as the fig ripens.

Examples of Plant Pathogenic Nematodes

Major Pests on Corn
    *Belonolaimus* (The Sting Namatode)
    *Criconemoides* (Ring Nematodes)
    *Helicotylenchu* (Spiral Nematodes)
    *Heterodera Zeae* (The Corn Cyst Nematode)
    *Hoplolaimus* (The Lance Nematode)
    *Xiphinema* (The Dagger Nematode)
    *Longidorus* (The Needle Nematode)
    *Meloidogyne* (The Root-Knot Nematodes)
    *Pratylenchus* (The Lesion Nematode)
    *Paratrichodorus* (Stubby-Root Nemadoes)
    *Tylenchorhynchus* (Stunt Nematodes)

Major Pests on Potato
    *Meloidogyne Chitwoodi* (Columbia Root-knot Nematode)
    *Meloidogyne Hapla* (Northern Root Knot Nematode)
    *Globodera Pallida* (Pale Potato Cyst Nematode)
    *Globodera Rostochiensis* (Golden Nematode)
    *Ditylenchus Destructor* (Potato Rot Nematode)

Major Pests on Soybean
    *Heterodera Glycines* (Soybean Cyst Nematode (SCN))
    *Belonolaimus* spp. (The Sting Nematode)

Major Pests on Sugar Beet
    *Heterodera Schachtti* (Sugar Beet Cyst Nematode)
    *Nacobbus Aberrans* (False Root-Knot Nematode)

Major Pests on Turf
    *Belonolaimus* Species (The Sting Nematodes)
    *Meloidogyne* Species (The Root-knot Nematodes)
    *Hoplolaimus Galeatus* (The Lance Nematode)
    *Criconemoides* Species (Ring Nematode)

Major Pests of Trees, Orchards and Vineyards
    *Bursaphelenchus Xylophilus* (Pine Wilt Nematode)
    *Radopholus Similis* (Burrowing Nematode)
    *Xiphinema Americanum* (The Dagger Nematode)
    *Meloidogyne Hapla* (Root-knot Nematode)
    *Rotylenchulus* spp. (Reniform Nematode)
    *Tylenchulus Semipenetrans* (The Citrus Nematode)
    *Belonolaimus Longicaudatus* (Ring Nematode)
    *Macroposthonia Xenoplax* (Ring Nematode)
    *Tylenchorhynchus* spp. (Stunt Nematodes)
    *Pratylenchus* spp. (Lesion Nematode)

Major Pests of Ornamentals and Garden Vegetables
   *Aphelenchoides* spp. (Foliar Nematodes)
   *Ditylenchus dipsaci* (Stem and Bulb Nematode)
   *Meloidogyne* spp. (Root-knot Nematodes)
   *Belonolaimus Longicaudatus* (Sting Nematode)
Phytophthora

*Phytophthora* (from Greek phyton, "plant" and phthorá, "destruction"; "the plant-destroyer") is a genus of plant-damaging Protists of the *Oomycetes* (water molds).

*Phytophthoras* are mostly pathogens of dicotyledons, and are relatively host-specific parasites. Many species of *Phytophthora* are plant pathogens of considerable economic importance. *Phytophthora infestans* was the infective agent of the potato blight that caused the Great Irish Famine (1845-1849). Plant diseases caused by this genus are difficult to control chemically, thus resistant cultivars are grown as a management strategy. Research beginning in the 1990s has placed some of the responsibility for European forest dieback on the activity of imported Asian *Phytophthoras*.

Other important *Phytophthora* diseases are:
   *Phytophthora alni*—causes alder root rot
   *Phytophthora cactorum*—causes rhododendron root rot affecting rhododendrons, azaleas and causes bleeding canker in hardwood trees
   *Phytophthora cinnamomi*—causes cinnamon root rot affecting woody ornamentals including arborvitae, azalea, *Chamaecyparis*, dogwood, forsythia, Fraser fir, hemlock, Japanese holly, juniper, *Pieris*, rhododendron, Taxus, white pine, and American chestnut
   *Phytophthora fragariae*—causes red root rot affecting strawberries
   *Phytophthora kernoviae*—pathogen of beech and rhododendron, also occurring on other trees and shrubs including oak, and holm oak. First seen in Cornwall, UK, in 2003.
   *Phytophthora palmivora*—causes fruit rot in coconuts and betel nuts
   *Phytophthora ramorum*—infects over 60 plant genera and over 100 host species—causes Sudden Oak Death
   *Phytophthora quercina*—causes oak death
   *Phytophthora sojae*—causes soybean root rot
Fusarium

*Fusarium* is a large genus of filamentous fungi widely distributed in soil and in association with plants. It is found in normal mycoflora of commodities, such as rice, bean, soybean, and other crops. While most species are more common at tropical and subtropical areas, some inhabit soil in cold climates. Some *Fusarium* species have a teleomorphic state Most species are harmless saprobes and are relatively abundant members of the soil microbial community. Some species produce mycotoxins in cereal crops that can affect human and animal health if they enter the food chain. The main toxins produced by these *Fusarium* species are fumonisins and trichothecenes.

The genus includes a number of economically important plant pathogenic species. *Fusarium graminearum* commonly infects barley if there is rain late in the season. It is of economic impact to the malting and brewing industries as well as feed barley. *Fusarium* contamination in barley can result in head blight and in extreme contaminations the barley can appear pink. The genome of this wheat and maize pathogen has been sequenced. *Fusarium graminearum* can also cause root rot and seedling blight. The total losses in the US of barley and wheat crops between 1991 and 1996 have been estimated at $3 billion.

*Fusarium* blight associated with turfgrass is caused by the widespread fungi *Fusarium roseum* and *F. tricinctum*.

*Fusarium* root rot is one of the most common diseases of conifer seedlings in the world and is widespread in North American nurseries.

*Fusarium* wilt affects many different horticultural plants and is the most important pathological problem of plants grown in artificial growing media. Because this fungus prefers warmer temperatures, heated container nurseries are ideal for build-up of this disease.

Solanaceous crop plants (tomato, potato, pepper, and eggplant) may be infected at any age by the fungi that cause *Fusarium wilt* and *Verticillium* wilt. The wilt organisms usually enter the plant through young roots and then grow into and up the water conducting vessels of the roots and stem. As the vessels are plugged and collapse, the water supply to the leaves is blocked. With a limited water supply, leaves begin to wilt on sunny days and recover at night.
Pythium

*Pythium* is a genus of parasitic oomycete. Because this group of organisms were once classified as fungi, they are sometimes still treated as such.

*Pythium* root rot is a common crop disease caused by a genus of organisms called "*Pythium*". These are commonly called water moulds. *Pythium* damping off is a very common problem in fields and greenhouses, where the organism kills newly emerged seedlings. This disease complex usually involves other pathogens such as *Phytophthora* and *Rhizoctonia*. *Pythium* wilt is caused by zoospore infection of older plants leading to biotrophic infections that become necrotrophic in response to colonization/reinfection pressures or environmental stress, leading to minor or severe wilting caused by impeded root functioning.

*Pythium* in turfgrass. Many *Pythium* species, along with their close relatives, *Phytophthora* species are plant pathogens of economic importance in agriculture. *Pythium* spp. tend to be very generalistic and unspecific in their host range. They infect a large range of hosts, while *Phytophthora* spp. are generally more host-specific.

For this reason, *Pythium* spp. are more devastating in the root rot they cause in crops, because crop rotation alone will often not eradicate the pathogen (nor will fallowing the field, as *Pythium* spp. are also good saprotrophs, and will survive for a long time on decaying plant matter).

It has been noted that in field crops, damage by *Pythium* spp. is often limited to the area affected, as the motile zoospores require ample surface water to travel long distances. Additionally, the capillaries formed by soil particles act as a natural filter and effectively trap many zoospores. However, in hydroponic systems inside greenhouses, where extensive monocultures of plants are maintained in plant nutrient solution (containing nitrogen, potassium, phosphate, and micro-nutrients) that is continuously recirculated to the crop, *Pythium* spp. cause extensive and devastating root rot and is often difficult to prevent or control. The root rot affects entire operations (tens of thousands of plants, in many instances) within two to four days due to the inherent nature of hydroponic systems where roots are nakedly exposed to the water medium, in which the zoospores can move freely.

Several *Pythium* species, including *P. oligandrum, P. nunn, P. periplocum*, and *P. acanthicum* are mycoparasites of plant pathogenic fungi and oomycetes, and have received interest as potential biocontrol agents.
Rhizoctonia

*Rhizoctonia* is plant pathogenic fungus with a wide host range and worldwide distribution. *Rhizoctonia* species consists of a large diverse group. All of them exist primarily as a sterile mycelium. It causes serious diseases on many hosts affecting plant parts that develop in the ground. These plant hosts include vegetables, ornamentals, turf grasses, and flowers. *Rhizoctonia solani*, the most important one, contains several nuclei in the mycelium cells. The fungus may sometimes exist as small brown sclerotia.

The most common symptom caused by *Rhizoctonia* is damping-off, which affects mainly seedlings but it can persist in plants that have survived damping-off to reveal other symptoms. On younger seedlings the disease causes the stem to become watery and soft, unable to support the seedling. Older seedlings may show lesions in the outer cortex that eventually girdle the stem.

Seedling stem canker caused by *Rhizoctonia* occurs on tobacco, cotton and other seedlings under conditions that are less favorable to the disease and where the seedlings manage to survive the damping-off stage. Root lesions are formed on plants from the seedling to mature stages. This leads to yellowing and serious weakening of the plant. Plants may also die.

On tubers, fleshy stems and roots as well as on bulbs *Rhizoctonia* causes brown rotten areas of various depths. These areas eventually dry to form a sunken area. Crater rot occurs on carrots and black scurf on potato tubers.

In turf grasses *Rhizoctonia* manifests itself as brown spot with circular brown patches in which the grass blades dry out.

*Rhizoctonia* overwinters as mycelia or sclerotia in soil or in plant material.

Sclerotinia

*Sclerotinia* is a genus of fungi in the family Sclerotiniaceae. In this genus *S. sclerotiorum* and *S. minor* cause many diseases such as molds, blights and rots in fruits, roots, stems leaves, flowers, bulbs and corms. They infect plants in all stages of growth. External symptoms of the disease often manifest as lesions on the plant stem followed by a white cottony mycelial growth and later the formation black sclerotia. Sclerotia may also form in the pith of the stem. *Sclerotinia homeocarpa* is the cause of dollar spot on turf.

*Sclerotinia sclerotiorum* overwinters as sclerotia on or in infected plant tissues, on the ground or as mycelium on live plants.

Erwinia

*Erwinia* is a genus of Enterobacteriaceae bacteria containing mostly plant pathogenic species which was named for the first phytobacteriologist, Erwin Smith. It is a gram negative bacterium related to *E. coli, Shigella, Salmonella* and *Yersinia*. It is primarily a rod-shaped bacteria. A well-known member of this genus is the species *E. amylovora*, which causes fireblight on apple, pear, and other Rosaceous crops. *Erwinia carotovora* (now known as *Pectobacterium carotovorum*) is another species, which causes diseases in many plants. These species produce enzymes that hydrolyze pectin between individual plant cells. This causes the cells to separate, a disease plant pathologists term plant rot.

*Erwinia* carotovora (*Pectobacterium carotovorum*). This bacteria is a plant pathogen with a wide host range (carrot, potato, tomato, leafy greens, squash and other cucurbits, onion, green peppers, etc.), able to cause disease in almost any plant tissue it invades. It is a very economically important pathogen in terms of postharvest losses, and a common cause of decay in stored fruits and vegetables. Decay caused by *E. carotovora* is often referred to as bacterial soft rot (BSR). Most plants or plant parts can resist invasion by the bacteria, unless some type of wound is present. High humidity and temperatures around 30° C. favor development of decay. Mutants can be produced which are less virulent. Virulence factors include: pectinases, cellulases, (which degrade plant cell walls), and also proteases, lipases, xylanases and nucleases (along with the normal virulence factors for pathogens—Fe acquisition, LPS integrity, multiple global regulatory systems).

Verticillium

*Verticillium* is a genus of fungi in the division Ascomycota. Within the genus, diverse groups are formed comprising saprotrophs and parasites of higher plants, insects, nematodes, mollusc eggs and other fungi thus it can be seen that the genus is a wide ranging group of taxa characterised by simple but ill-defined characters. The genus may be broadly divided into three ecologically based groups 1) mycopathogens; 2) entomopathogens; and 3) plant pathogens and related saprotrophs. However, recently the genus has undergone some revision into which most entomopathogenic and mycopathogenic isolates fall into a new group called *Lecanicillium*. Plant pathogenic isolates still retain the original genus name *Verticillium*.

The better known species of *Verticillium* are, *V. dahliae* and *V. albo-atrum* that cause a wilt disease called *Verticillium* wilt in more than 300 eudicot plant species.

Drip Irrigation

Drip irrigation, also known as trickle irrigation or micro-irrigation, is an irrigation method which minimizes the use of water and fertilizer or any other additive by allowing water to drip slowly to the roots of plants, either onto the soil surface or directly onto the root zone, through a network of valves, pipes, tubing, and emitters.

Drip irrigation has arguably become the world's most valued innovation in agriculture since the invention of the impact sprinkler in the 1930s, which replaced flood irrigation. Drip irrigation may also use devices called micro-spray heads, which spray water in a small area, instead of dripping emitters. These are generally used on tree and vine crops with wider root zones. Subsurface drip irrigation (SDI) uses permanently or temporarily buried dripperline or drip tape located at or below the plant roots. It is becoming popular for row crop irrigation, especially in areas where water supplies are limited or recycled water is used for irrigation. Careful study of all the relevant factors like land topography, soil, water, crop and agro-climatic conditions are needed to determine the most suitable drip irrigation system and components to be used in a specific installation.

Deep percolation, where water moves below the root zone, can occur if a drip system is operated for too long of a duration or if the delivery rate is too high. Drip irrigation methods range from very high-tech and computerized to low-tech and labor-intensive. Lower water pressures are usually needed than for most other types of systems, with the exception of low energy center pivot systems and surface irrigation systems, and the system can be designed for uniformity throughout a field or for precise water delivery to individual plants in a landscape containing a mix of plant species. Although it is difficult to regulate pressure on steep slopes, pressure compensating emitters are available, so the field does not have to be level. High-tech solutions involve precisely calibrated emitters located along lines of tubing that extend from a computerized set of valves. Both pressure regulation and filtration to remove particles are important. The tubes are usually black (or buried under soil or mulch) to prevent the growth of algae and to protect the polyethylene from degradation due to ultraviolet light. But drip irrigation can also be as low-tech as a porous clay vessel sunk into the soil and occasionally filled from a hose or bucket. Subsurface drip irrigation has been used successfully on lawns, but it is more expensive than a more traditional sprinkler system.

Sprinkler Irrigation

In sprinkler or overhead irrigation, water is piped to one or more central locations within the field and distributed by overhead high-pressure sprinklers or guns. A system utilizing sprinklers, sprays, or guns mounted overhead on permanently installed risers is often referred to as a solid-set irrigation system. Higher pressure sprinklers that rotate are called rotors and are driven by a ball drive, gear drive, or impact mechanism. Rotors can be designed to rotate in a full or partial circle. Guns are similar to rotors, except that they generally operate at very high pressures of 40 to 130 lbf/in$^2$ (275 to 900 kPa) and flows of 50 to 1200 US gal/min (3 to 76 L/s), usually with nozzle diameters in the range of 0.5 to 1.9 inches (10 to 50 mm). Guns are used not only for irrigation, but also for industrial applications such as dust suppression and logging.

Sprinklers may also be mounted on moving platforms connected to the water source by a hose. Automatically moving wheeled systems known as traveling sprinklers may irrigate areas such as small farms, sports fields, parks, pastures, and cemeteries unattended. Most of these utilize a length of polyethylene tubing wound on a steel drum. As the tubing is wound on the drum powered by the irrigation water or a small gas engine, the sprinkler is pulled across the field. When the sprinkler arrives back at the reel the system shuts off. This type of system is known to most people as a "waterreel" traveling irrigation sprinkler and they are used extensively for dust suppression, irrigation, and land application of waste water. Other travelers use a flat rubber hose that is dragged along behind while the sprinkler platform is pulled by a cable.

Center pivot irrigation is a form of sprinkler irrigation consisting of several segments of pipe (usually galvanized steel or aluminum) joined together and supported by trusses, mounted on wheeled towers with sprinklers positioned along its length. The system moves in a circular pattern and is fed with water from the pivot point at the center of the arc.

Most center pivot systems now have drops hanging from a u-shaped pipe called a gooseneck attached at the top of the pipe with sprinkler heads that are positioned a few feet (at most) above the crop, thus limiting evaporative losses. Drops can also be used with drag hoses or bubblers that deposit the water directly on the ground between crops. The crops are planted in a circle to conform to the center pivot. This type of system is known as LEPA (Low Energy Precision Application).

Hydroponics

Hydroponics (from the Greek words hydro water and ponos labor) is a method of growing plants using mineral nutrient solutions, without soil. Terrestrial plants may be grown with their roots in the mineral nutrient solution only or in an inert medium, such as perlite, gravel, or mineral wool.

Plant physiology researchers discovered in the 19th century that plants absorb essential mineral nutrients as inorganic ions in water. In natural conditions, soil acts as a mineral nutrient reservoir but the soil itself is not essential to plant growth. When the mineral nutrients in the soil dissolve in water, plant roots are able to absorb them. When the required mineral nutrients are introduced into a plant's water supply artificially, soil is no longer required for the plant to thrive. Almost any terrestrial plant will grow with hydroponics.

The two main types of hydroponics are solution culture and medium culture. Solution culture does not use a solid medium for the roots, just the nutrient solution. The three main types of solution culture are static solution culture, continuous flow solution culture and aeroponics. The medium culture method has a solid medium for the roots and is named for the type of medium, e.g. sand culture, gravel culture or rockwool culture. There are two main variations for each medium, subirrigation and top irrigation. For all techniques, most hydroponic reservoirs are now built of plastic but other materials have been used including concrete, glass, metal, vegetable solids and wood. The containers should exclude light to prevent algae growth in the nutrient solution.

In static solution culture, plants are grown in containers of nutrient solution, such as glass Mason jars (typically in-home applications), plastic buckets, tubs or tanks. The solution is usually gently aerated but may be unaerated. If unaerated, the solution level is kept low enough that enough roots are above the solution so they get adequate oxygen. A hole is cut in the lid of the reservoir for each plant. There can be one to many plants per reservoir. Reservoir size can be increased as plant size increases. A homemade system can be constructed from plastic food containers or glass canning jars with aeration provided by an aquarium pump, aquarium airline tubing and aquarium valves. Clear containers are covered with aluminium foil, butcher paper, black plastic or other material to exclude light, thus helping to eliminate the formation of algae. The nutrient solution is either changed on a schedule, such as once per week, or when the concentration drops below a certain level as determined with an electrical conductivity meter. Whenever the solution is depleted below a certain level, either water or fresh nutrient solution is added. A Mariotte's bottle can be used to automatically maintain the solution level. In raft solution culture, plants are placed in a sheet of buoyant plastic that is floated on the surface of the nutrient solution. That way, the solution level never drops below the roots.

In continuous flow solution culture the nutrient solution constantly flows past the roots. It is much easier to automate than the static solution culture because sampling and adjustments to the temperature and nutrient concentrations can be made in a large storage tank that serves potentially thousands of plants. A popular variation is the nutrient film technique or NFT whereby a very shallow stream of water containing all the dissolved nutrients required for plant growth is recirculated past the bare roots of plants in a watertight gully, also known as channels. Ideally, the depth of the recirculating stream should be very shallow, little more than a film of water, hence the name 'nutrient film'. This ensures that the thick root mat, which develops in the bottom of the channel, has an upper surface which, although moist, is in the air. Subsequently, there is an abundant supply of oxygen to the roots of the plants. A properly designed NFT system is based on using the right channel slope, the right flow rate and the right channel length. The main advantage of the NFT system over other forms of hydroponics is that the plant roots are exposed to adequate supplies of water, oxygen and nutrients. In all other forms of production there is a conflict between the supply of these requirements, since excessive or deficient amounts of one results in an imbalance of one or both of the others. NFT, because of its design, provides a system where all three requirements for healthy plant growth can be met at the same time, providing the simple concept of NFT is always remembered and practised. The result of these advantages is that higher yields of high quality produce are obtained over an extended period of cropping.

The same design characteristics apply to all conventional NFT systems. While slopes along channels of 1:100 have been recommended, in practice it is difficult to build a base for channels that is sufficiently true to enable nutrient films to flow without ponding in locally depressed areas. Consequently, it is recommended that slopes of 1:30 to 1:40 are used. This allows for minor irregularities in the surface but, even with these slopes, ponding and waterlogging may occur. The slope may be provided by the floor, or benches or racks may hold the channels and provide the required slope. Both methods are used and depend on local requirements, often determined by the site and crop requirements.

As a general guide, flow rates for each gully should be 1 liter per minute. At planting, rates may be half this and the upper limit of 2 L/min appears about the maximum. Flow rates beyond these extremes are often associated with nutritional problems. Depressed growth rates of many crops have been observed when channels exceed 12 meters in length. On rapidly growing crops, tests have indicated that, while oxygen levels remain adequate, nitrogen may be depleted over the length of the gully. Consequently, channel length should not exceed 10-15 meters. In situations where this is not possible, the reductions in growth can be eliminated by placing another nutrient feed halfway along the gully and reducing flow rates to 1 L/min through each outlet.

Aeroponics is a system where roots are continuously or discontinuously kept in an environment saturated with fine drops (a mist or aerosol) of nutrient solution. The method requires no substrate and entails growing plants with their roots suspended in a deep air or growth chamber with the roots periodically wetted with a fine mist of atomized nutrients. Excellent aeration is the main advantage of aeroponics.

Aeroponic techniques have proved to be commercially successful for propagation, seed germination, seed potato production, tomato production, leaf crops and micro-greens.

An advantage of aeroponics over hydroponics is that any species of plants can be grown in a true aeroponic system because the micro environment of an aeroponic can be finely controlled. The limitation of hydroponics is that only certain species of plants can survive for so long in water before they become water logged. The advantage of aeroponics is due to the fact that suspended aeroponic plants receive 100% of the available oxygen and $CO_2$ to the roots zone, stems and leaves, thus accelerating biomass growth and reducing rooting times.

Passive subirrigation, also known as passive hydroponics or semi-hydroponics, is a method where plants are grown in an inert porous medium that transports water and fertilizer to the roots by capillary action from a separate reservoir as necessary, reducing labor and providing a constant supply of water to the roots. In the simplest method, the pot sits in a shallow solution of fertilizer and water or on a capillary mat saturated with nutrient solution. The various hydroponic media available, such as expanded clay and coconut husk, contain more air space than more traditional potting mixes, delivering increased oxygen to the roots, which is important in epiphytic plants such as orchids and bromeliads, whose roots are exposed to the air in nature. Additional advantages of passive hydroponics are the reduction of root rot and the additional ambient humidity provided through evaporation.

Plant nutrients are dissolved in the water used in hydroponics and are mostly in inorganic and ionic form. Primary among the dissolved cations (positively-charged ions) are $Ca^{2+}$ (calcium), $Mg^{2+}$ (magnesium), and $K^+$ (potassium); the major nutrient anions in nutrient solutions are $NO_3^-$ (nitrate), $SO_4^{2-}$ (sulfate), and $H_2PO_4^-$ (dihydrogen phosphate).

Numerous recipes for hydroponic solutions are available. Many use different combinations of chemicals to reach similar total final compositions. Commonly-used chemicals for the macronutrients include potassium nitrate, calcium nitrate, potassium phosphate, and magnesium sulfate. Various micronutrients are typically added to hydroponic solutions to supply essential elements; among them are Fe (iron), Mn (manganese), Cu (copper), Zn (zinc), B (boron), Cl (chlorine), and Ni (nickel). Chelating agents are sometimes used to keep Fe soluble. Variation of different mixes throughout the plant life cycle, further optimizes its nutritional value.

Plants will change the composition of the nutrient solutions upon contact by depleting specific nutrients more rapidly than others, removing water from the solution, and altering the pH by excretion of either acidity or alkalinity. Care is required not to allow salt concentrations to become too high, nutrients to become too depleted, or pH to vary from the desired value.

Agricultural Water Use and Soil Wetting

For crop irrigation, optimal water efficiency means minimizing losses due to evaporation, runoff or fast vertical penetration of water through the soil. An Evaporation pan can be used to determine how much water is required to irrigate the land. Flood irrigation, the oldest and most common type of irrigation, is often very uneven in distribution, as parts of a field may receive excess water in order to deliver sufficient quantities to other parts. Overhead irrigation, using center-pivot or lateral-moving sprinklers, gives a much more equal and controlled distribution pattern, but in extremely dry conditions, much of the water may evaporate before it reaches the ground. Drip irrigation offers the best results in delivering water to plant roots with minimal losses.

As changing irrigation systems can be a costly undertaking, conservation efforts often concentrate on maximizing the efficiency of the existing system. This may include chiseling compacted soils, creating furrow dikes to prevent runoff, and using soil moisture and rainfall sensors to optimize irrigation schedules. Water conservation efforts include but are not limited to the following:

Recharge pits, which capture rainwater and runoff and use it to recharge ground water supplies. This helps in the formation of ground water wells etc. and eventually reduces soil erosion caused due to running water.

Any beneficial reduction in water loss, use, or waste.

A reduction in water use accomplished by implementation of water conservation or water efficiency measures.

Improved water management practices that reduce or enhance the beneficial use of water. A water conservation measure is an action, behavioral change, device, technology, or improved design or process implemented to reduce water loss, waste, or use. Water efficiency is a tool of water conservation. That results in more efficient water use and thus reduces water demand. The value and cost-effectiveness of a water efficiency measure must be evaluated in relation to its effects on the use and cost of other natural resources (e.g. energy or chemicals).

As discussed above, drip irrigation is now very popular. Unfortunately, water applied via drip irrigation tends to channel to below useful depths. The compositions of the instant invention have the surprising effect of reducing channeling by causing wetting of treated soil in a horizontal instead of vertical fashion. This increases the amount of water available to the roots of plants and decreases the total amount of water that must be used for irrigation leading to water savings and reduced agricultural water consumption. At least 33% and up to 55% less water is required.

Infiltration

Infiltration is the process by which water on the ground surface enters the soil. Infiltration rate in soil science is a measure of the rate at which soil is able to absorb rainfall or irrigation. It is measured in inches per hour or millimeters per hour. The rate decreases as the soil becomes saturated. If the precipitation rate exceeds the infiltration rate, runoff will usually occur unless there is some physical barrier. It is related to the saturated hydraulic conductivity of the near-surface soil. The rate of infiltration can be measured using an infiltrometer.

Infiltration is governed by two forces: gravity and capillary action. While smaller pores offer greater resistance to gravity, very small pores pull water through capillary action in addition to and even against the force of gravity.

The rate of infiltration is affected by soil characteristics including ease of entry, storage capacity, and transmission rate through the soil. The soil texture and structure, vegetation types and cover, water content of the soil, soil temperature, and rainfall intensity all play a role in controlling infiltration rate and capacity. For example, coarse-grained sandy soils have large spaces between each grain and allow water to infiltrate quickly. Vegetation creates more porous soils by both protecting the soil from pounding rainfall, which can close natural gaps between soil particles, and loosening soil through root action. This is why forested areas have the highest infiltration rates of any vegetative types.

The top layer of leaf litter that is not decomposed protects the soil from the pounding action of rain, without this the soil can become far less permeable. In chapparal vegetated areas, the hydrophobic oils in the succulent leaves can be spread over the soil surface with fire, creating large areas of hydrophobic soil. Other conditions that can lower infiltration rates or block them include dry plant litter that resists re-wetting, or frost. If soil is saturated at the time of an intense freezing period, the soil can become a concrete frost on which almost no infiltration would occur. Over an entire watershed, there are likely to be gaps in the concrete frost or hydrophobic soil where water can infiltrate.

Once water has infiltrated the soil it remains in the soil, percolates down to the ground water table, or becomes part of the subsurface runoff process.

The process of infiltration can continue only if there is room available for additional water at the soil surface. The available volume for additional water in the soil depends on the porosity of the soil and the rate at which previously infiltrated water can move away from the surface through the soil. The maximum rate that water can enter a soil in a given condition is the infiltration capacity. If the arrival of the water at the soil surface is less than the infiltration capacity, all of the water will infiltrate. If rainfall intensity at the soil surface occurs at a rate that exceeds the infiltration capacity, ponding begins and is followed by runoff over the ground surface, once depression storage is filled. This runoff is called Horton overland flow. The entire hydrologic system of a watershed is sometimes analyzed using hydrology transport models, mathematical models that consider infiltration, runoff and channel flow to predict river flow rates and stream water quality.

Infiltration is a component of the general mass balance hydrologic budget. There are several ways to estimate the volume and/or the rate of infiltration of water into a soil. Three excellent estimation methods are the Green-Ampt method, SCS method, Horton's method, and Darcy's law.

General hydrologic budget. The general hydrologic budget, with all the components, with respect to infiltration F. Given all the other variables and infiltration is the only unknown, simple algebra solves the infiltration question.

$$F = B_I + P - E - T - ET - S - R - I_A - B_O$$

where
F is infiltration, which can be measured as a volume or length;
$B_I$ is the boundary input, which is essentially the output watershed from adjacent, directly connected impervious areas;
$B_O$ is the boundary output, which is also related to surface runoff, R, depending on where one chooses to define the exit point or points for the boundary output;
P is precipitation;
E is evaporation;
ET is evapotranspiration;
S is the storage through either retention or detention areas;
$I_A$ is the initial abstraction, which is the short term surface storage such as puddles or even possibly detention ponds depending on size;
R is surface runoff.

The only note on this method is one must be wise about which variables to use and which to omit, for doubles can easily be encountered. An easy example of double counting variables is when the evaporation, E, and the transpiration, T, are placed in the equation as well as the evapotranspiration, ET. ET has included in it T as well as a portion of E.

Green-Ampt. Named for two men; Green and Ampt. The Green-Ampt method of infiltration estimation accounts for many variables that other methods, such as Darcy's law, do not. It is a function of the soil suction head, porosity, hydraulic conductivity and time.

$$\int_0^{F(t)} \frac{1 - \psi \Delta \theta}{F + \psi \Delta \theta} dF = \int_0^t K dt$$

where
$\psi$ is wetting front soil suction head;
$\theta$ is water content;
K is Hydraulic conductivity;
F is the total volume already infiltrated.

Once integrated, one can easily choose to solve for either volume of infiltration or instantaneous infiltration rate:

$$F(t) = Kt + \psi \Delta \theta \ln\left[1 + \frac{F(t)}{\psi \Delta \theta}\right].$$

Using this model one can find the volume easily by solving for F(t). However the variable being solved for is in the equation itself so when solving for this one must set the variable in question to converge on zero, or another appropriate constant. A good first guess for F is Kt. The only note on using this formula is that one must assume that $h_0$, the water head or the depth of ponded water above the surface, is negligible. Using the infiltration volume from this equation one may then substitute F into the corresponding infiltration rate equation below to find the instantaneous infiltration rate at the time, t, F was measured.

$$f(t) = K\left[\frac{\psi \Delta \theta}{F(t)} + 1\right].$$

Horton's equation. Horton's equation is another viable option when measuring ground infiltration rates or volumes. It is an empirical formula that says that infiltration starts at a constant rate, $f_0$, and is decreasing exponentially with time, t. After some time when the soil saturation level reaches a certain value, the rate of infiltration will level off to the rate $f_c$.

$$f_t = f_c + (f_0 - f_c)e^{-kt}$$

Where
$f_t$ is the infiltration rate at time t;
$f_0$ is the initial infiltration rate or maximum infiltration rate;
$f_c$ is the constant or equilibrium infiltration rate after the soil has been saturated or minimum infiltration rate;
k is the decay constant specific to the soil.

The other method of using Horton's equation is as below. It can be used to find the total volume of infiltration, F, after time t.

$$F_t = f_c t + \frac{(f_0 - f_c)}{k}(1 - e^{-kt})$$

Kostiakov equation. Named after its founder Kostiakov is an empirical equation which assumes that the intake rate declines over time according to a power function.

$$f(t) = ake^{a-1}$$

Where a and k are empirical parameters.

The major limitation of this expression is its reliance on the zero final intake rate. In most cases the infiltration rate instead approaches a finite steady value, which in some cases may occur after short periods of time. The Kostiakov-Lewis variant, also known as the "Modified Kostiakov" equation corrects for this by adding a steady intake term to the original equation.

$$f(t) = ake^{a-1} + f_0$$

in integrated form the cumulative volume is expressed as:

$$F(t) = kt^a + f_0 t$$

Where $f_0$ approximates, but does not necessarily equate to the final infiltration rate of the soil.

Darcy's law. This method used for infiltration is using a simplified version of Darcy's law. In this model the ponded water is assumed to be equal to $h_0$ and the head of dry soil that exists below the depth of the wetting front soil suction head is assumed to be equal to $-\psi - L$.

$$f = K\left[\frac{h_0 - (-\psi - L)}{L}\right]$$

where
$h_0$ is the depth of ponded water above the ground surface;
K is the hydraulic conductivity;
L is the total depth of subsurface ground in question.

In summary all of these equations should provide a relatively accurate assessment of the infiltration characteristics of the soil in question.

EXAMPLES

Method of application: 2 quarts to 5 gallons of the compositions described herein are injected, undiluted directly into the drip irrigation line system per acre. Volume calculation will depend on
1. Gallons of water per acre being applied
2. Pressure levels of nematodes and *phytophthora* expectations
3. Frequency of repeat applications Frequency of application: Ideally 3 to 5 days before planting. If this is not possible, then 10-14 days after planting. Repeat 3 to 5 weeks after planting and thereafter only if needed.

The compositions disclosed herein may have additional nutrients added from time to time by the manufacturer.

In such events the composition will be at 66.66% strength with the nutrients included in the 33.3% of the formula.

In such cases the application volume will be increased by 50%.

The invention claimed is:

1. A method of increasing wetted soil volume and killing plant pests selected from the group consisting of Nematodes, *Phytophthora, Fusarium, Pythium, Rhizoctonia, Sclerotinia, Erwinia* and *Verticillium* comprising:
   a) selecting soil in need of treatment;
   b) applying to the soil in need of treatment an effective amount of a composition comprising:
      i) one or more surfactants, wherein the surfactants are present in an amount of about 5% to about 20% by weight; and
      ii) one or more high terpene containing oils, wherein the high terpene containing oils are present in an amount of about 12% to about 20% by weight;
   wherein said one or more high terpene containing oils is selected from the group consisting of orange oil, lemon oil, lime oil, grapefruit oil and tangerine oil;
to thereby increase wetted soil volume of the soil selected for treatment and to kill said plant pests selected from the group consisting of Nematodes, *Phytophthora, Fusarium, Pythium, Rhizoctonia, Sclerotinia, Erwinia* and *Verticillium* in the soil selected for treatment.

2. The method of claim 1, wherein said selection step comprises identifying soil containing any one of said pests present in an amount sufficient to harm or reduce the growth of a plant growing in said soil.

3. The method of claim 1, wherein any one of said pests is present in an amount sufficient to reduce the yield of said plant.

4. The method of claim 1, wherein a prior planting in said soil resulted in the determination that any one of said pests are present in the soil in an amount sufficient to harm or reduce the growth of plants grown in said soil.

5. The method of claim 1, wherein said plant pest is *Phytophthora*.

6. The method of claim 1, wherein said plant pest is root-knot nematode.

7. The method of claim 1, wherein said composition is applied via drip irrigation.

8. The method of claim 1, wherein said composition is applied via sprinkler irrigation.

9. The method of claim 1, wherein said application is conducted prior to planting.

10. The method of claim 1, wherein said application is conducted after planting.

11. The method of claim 1, wherein said composition further comprises borax.

12. The method of claim 1, wherein said composition further comprises a fertilizer.

13. The method of claim 1, wherein said composition further comprises micro-nutrients.

14. The method of claim 1, wherein said water further comprises propylene glycol.

15. The method of claim 1, wherein said water further comprises sodium laureth sulfate.

16. The method of claim 1, wherein said water further comprises secondary alcohol ethoxylate.

17. The method of claim 1, wherein said water further comprises urea.

18. The method of claim 1, wherein said water further comprises ethylenediaminetetra-acetic acid (EDTA).

19. The method of claim 1, wherein said water further comprises methyl paraben.

20. The method of claim 1, wherein said water further comprises ethyl alcohol.

21. The method of claim 1, wherein said composition further comprises an insecticide, fungicide, herbicide, nematicide or acaricide.

22. A method for increasing wetted soil volume available for water uptake by plant roots comprising:
 a) selecting soil in need of treatment;
 b) applying to the soil in need of treatment an effective amount of a composition comprising:
  i) one or more surfactants, wherein the surfactants are present in an amount of about 5% to about 20% by weight; and
  ii) one or more high terpene based oils, wherein the high terpene based oils present in an amount of about 12% to about 20% by weight;
to thereby increase wetted soil volume available for water uptake by plant roots in the soil selected for treatment compared to untreated soil;
wherein said one or more high terpene based oils is selected from the group consisting of orange oil, lemon oil, lime oil, grapefruit oil and tangerine oil.

23. The method of claim 22, wherein the lateral movement of water in said soil is increased compared to the lateral movement of water in soil that has not been subjected to said treatment.

24. The method of claim 22, wherein said treatment increases the amount of water available to a plant growing in said soil by increasing the amount of water in the root zone of said plant compared to soil that has not been subjected to said treatment.

25. The method of claim 22, wherein said treated soil has at least 33% more wetted soil volume available for water uptake by the plant roots compared to untreated soil.

26. The method of claim 22, wherein said treated soil has at least a 25% more wetted soil volume available for water uptake by the plant roots compared to untreated soil.

27. The method of claim 22, wherein said composition is applied via drip irrigation.

28. The method of claim 22, wherein said composition is applied via sprinkler irrigation.

29. The method of claim 22, wherein said application is conducted prior to planting.

30. The method of claim 22, wherein said application is conducted after planting.

31. The method of claim 22, wherein said composition further comprises borax.

32. The method of claim 22, wherein said composition further comprises a fertilizer.

33. The method of claim 22, wherein said composition further comprises micro-nutrients.

34. The method of claim 22, wherein said water further comprises propylene glycol.

35. The method of claim 22, wherein said water further comprises sodium laureth sulfate.

36. The method of claim 22, wherein said water further comprises secondary alcohol ethoxylate.

37. The method of claim 22, wherein said water further comprises urea.

38. The method of claim 22, wherein said water further comprises ethylenediaminetetra-acetic acid (EDTA).

39. The method of claim 22, wherein said water further comprises methyl paraben.

40. The method of claim 22, wherein said water further comprises ethyl alcohol.

41. The method of claim 22, wherein said composition further comprises an insecticide, fungicide, herbicide, nematicide or acaricide.

* * * * *